United States Patent
Gunaratnam et al.

(10) Patent No.: US 6,412,487 B1
(45) Date of Patent: Jul. 2, 2002

(54) MASK CUSHION AND FRAME ASSEMBLY

(75) Inventors: Michael K. Gunaratnam, Marsfield; Gregory S. Smart, Randwick; Philip R. Kwok, Chatswood, all of (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/501,004

(22) Filed: Feb. 9, 2000

Related U.S. Application Data

(63) Continuation-in-part of application No. 29/115,618, filed on Dec. 16, 1999, and a continuation-in-part of application No. 09/316,227, filed on May 21, 1999, and a continuation-in-part of application No. 29/101,860, filed on Mar. 12, 1999, and a continuation-in-part of application No. 29/101,861, filed on Mar. 12, 1999, and a continuation-in-part of application No. 29/101,862, filed on Mar. 12, 1999, and a continuation-in-part of application No. 08/791,212, filed on Jan. 31, 1997, now Pat. No. 6,112,746.

(30) Foreign Application Priority Data

| Dec. 9, 1998 | (AU) | 3922/1998 |
| Dec. 9, 1998 | (AU) | 3923/1998 |
| Dec. 9, 1998 | (AU) | 3924/1998 |
| Feb. 9, 1999 | (AU) | 8550 |
| Jun. 18, 1999 | (AU) | 1040 |
| Jun. 18, 1999 | (AU) | 1916/1999 |

(51) Int. Cl.$^7$ ............................................. A62B 18/08
(52) U.S. Cl. ............................. 128/206.24; 128/205.25; 128/207.13
(58) Field of Search ................... 128/205.25, 206.24, 128/206.26, 207.13

(56) References Cited

U.S. PATENT DOCUMENTS

| 1,653,572 | A | * | 12/1927 | Jackson | 128/206.24 |
| 2,931,356 | A | * | 4/1960 | Schwarz | 128/206.24 |
| 4,807,617 | A | * | 2/1989 | Nesti | 128/205.25 |
| 5,003,633 | A | * | 4/1991 | Itoh | 128/206.24 |
| 5,538,001 | A | * | 7/1996 | Bridges | 128/205.25 |
| 5,794,617 | A | * | 8/1998 | Brunell et al. | 128/206.24 |
| 5,909,732 | A | * | 6/1999 | Diesel et al. | 128/206.24 |
| 6,082,360 | A | * | 7/2000 | Rudolph et al. | 128/206.24 |
| 6,196,223 | B1 | * | 3/2001 | Belfer et al. | 128/205.25 |

OTHER PUBLICATIONS

Respironics, Inc. "Nasal Mask System Silicone Contour Mask" Product Instructions, 2 pages, Jun., 1997.
ResMed, Mask Systems Product Brochure, 2 pages, Sep., 1992.

\* cited by examiner

*Primary Examiner*—Aaron J. Lewis
(74) *Attorney, Agent, or Firm*—Pillsbury Winthrop LLP

(57) ABSTRACT

A respiratory mask assembly includes a rigid mask frame (160) with a rim portion comprising a rearwardly projecting tongue (620) and lateral flange (640) and a cushion (180) having a rim with a corresponding groove (740) and a rearwardly facing shoulder (720). A clip in the form of a collar (800) passes over the cushion, engaging behind the shoulder (720), and has securing tabs (820) which engage recesses (660) in the flange (640).

5 Claims, 10 Drawing Sheets

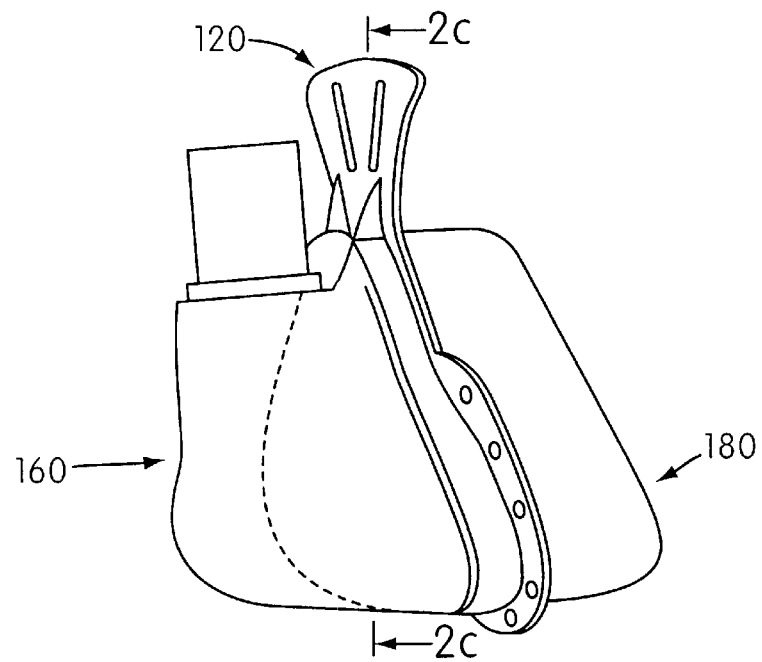
FIG. 2a
PRIOR ART
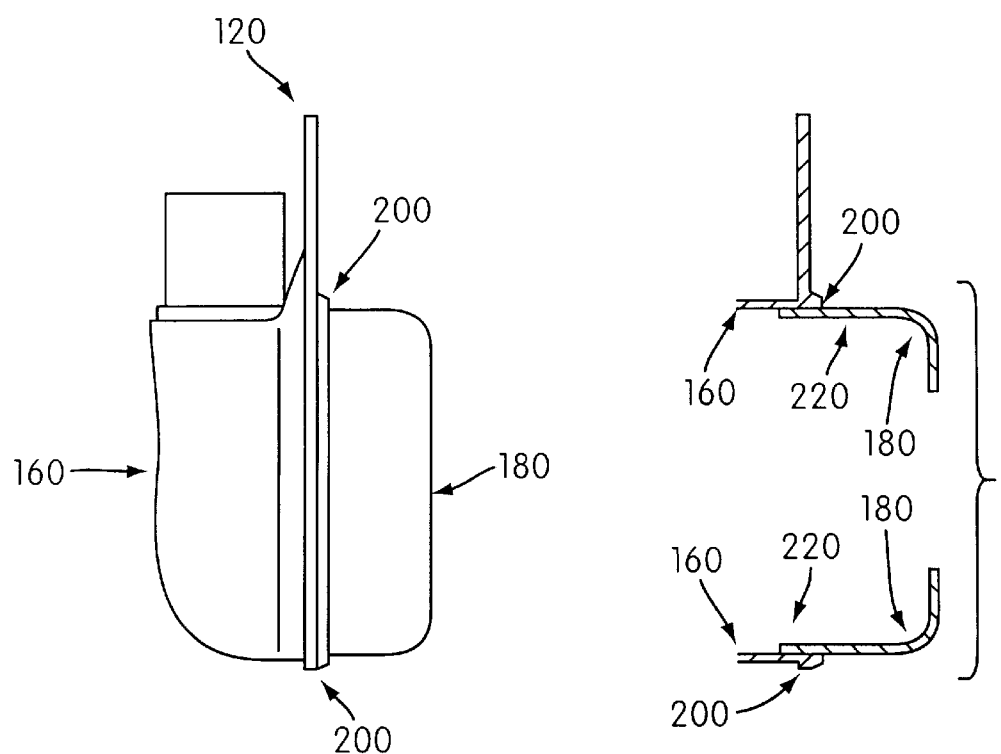
FIG. 2b
PRIOR ART
FIG. 2c
PRIOR ART

MASK CUSHION AND FRAME ASSEMBLY

This application is a Continuation-in-part application of U.S. patent application Ser. No. 09/498,705, filed Feb. 7, 2000, currently pending; U.S. patent application Ser. No. 09/316,227, filed May 21, 1999, currently pending; U.S. patent application Ser. No. 08/791,212, filed Jan. 31, 1997, now issued as U.S. Pat. No. 6,112,746; U.S. Design patent application Ser. No. 29/101,860, filed Mar. 12 1999, now U.S. Design Pat. No. D428,139; U.S. Design patent application Ser. No. 29/101,861 filed Mar. 12, 1999, now U.S. Design Pat. No. D430,663; U.S. Design patent application Ser. No. 29/101, 862 filed Mar. 12, 1999, now U.S. Design Pat. No. D428,988; and U.S. Design patent application Ser. No. 29/115,618 filed Dec. 16, 1999, now U.S. Design Pat. No. D443,355 the disclosures of which are hereby incorporated by reference.

FIELD OF THE INVENTION

The invention relates to a method and apparatus for connecting a nasal or fill-face mask cushion to a mask frame, where the mask is suitable for the delivery of breathable gases to a patient for the treatment of sleep disordered breathing (SDB).

BACKGROUND TO THE INVENTION

Nasal and fill-face masks systems suitable for the delivery of air or other breathable gases to patients for the treatment of sleep disordered breathing may include a mask (100), a forehead support (120) and headgear (140), as depicted in FIG. 1. The mask may comprise a rigid shell (160), termed a frame, and a soft portion (180), termed a cushion. The frame may be constructed from a material such as polycabonate, forming a cavity which overlies the patient's nose and/or mouth. The soft cushion may be constructed from a material such as silicone spacing the frame away from the patient's face to provide comfortable contact.

In the case of the Mirage® Mask (ResMed Limited), shown in FIG. 1, the headgear (140) is constructed from fabric and includes a rear portion which engages the region near the occiput of the patient, and four straps (145) which are secured to a forehead support (2 straps) and nasal mask frame (2 straps). The straps include hook and loop material, such as Velcro(™) on one side. The mask frame and forehead supports include loops through which straps can pass.

In one form of known mask, the cushion and frame are glued together, as shown in FIGS. 2a to 2c. FIG. 2c shows a cross-section 2c—2c through FIG. 2a. The frame (160) includes a rim portion (200) surrounding the rear aperture of the frame. There is a corresponding rim portion (220) on the cushion (180) which fits inside the rim (200) on the frame. The two rims (200, 220) are glued together. A disadvantage with this approach is that the cushion cannot easily be removed for separate cleaning from the frame. Furthermore, there is an increased manufacturing cost since gluing requires assembly time and adhesive.

In one known mask the Modular mask system (ResMed Limited), the frame and cushion are held together using a tongue (300) and groove (320), as depicted in FIGS. 3a to 3c. The frame (160) is generally triangular in front view. In use, the front of the frame faces away form the patient and the back of the frame faces towards the patient. The rim portion (350) on the frame (160) includes an outwardly extending flange (340) and engages with a corresponding rim (360) on the cushion (180), such that the rims (350, 360) confront along a locus lying generally in the plane of the patient's face. The frame rim (350) further includes a tongue (300) which protrudes rearwardly from the back of the frame and is received in a corresponding complementary shaped groove (320) formed in rim portion (360) of the cushion (180). In addition, the rim (350) of the frame (160) and the rim (360) of the cushion (180) include aligned slots (380) through which headgear straps (145) can pass. Hence the slots (380) and straps (145) make a contribution to holding the frame (160) and cushion (180) together, in addition to the use of the tongue (300) and groove (320).

In another known mask, a tongue and groove mechanism is used to hold the frame (160) and cushion (180) together, and the tongue (500), which is positioned on the frame (160) has an irregular cross-section as depicted in FIGS. 4a to 4c. The side (520) of the tongue (500) on the interior of the frame (160) is flat. The other side (540) of the tongue (500) has a lateral projection (560) approximately at right angles to the tongue (500). The groove (580) of the cushion (180) has a complementary shape, including a lateral recess (585) for receiving projection (560). The connection relies on the elasticity of the cushion to retain the cushion in place.

The present invention to provide an improved arrangement.

SUMMARY OF THE INVENTION

The present invention provides a respiratory mask assembly for delivering breathable gas to a patient, comprising (i) a substantially rigid mask fame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which engages the mask frame so as to retain the mask cushion on the mask frame.

Preferably, the clip's securing means includes at least one securing tab which engages a respective recess in the mask frame, and more preferably on a lateral flange of rim portion of the fame.

Preferably also, the clip is formed as a collar member having a plurality of tabs angularly spaced about the collar member, and the mask frame has a respective plurality of the recesses.

BRIEF DESCRIPTION OF THE DRAWINGS

FIG. 2a shows a perspective view of a form of prior art mask frame and cushion which are glued together FIG. 2b shows a side view of the mask shown in FIG. 2a.

FIG. 2c shows a cross-sectional view of the mask shown in FIG. 2a.

FIG. 3b shows a side view of the mask shown in FIG. 3a.

FIG. 3c shows a crosssectional view of the mask shown in FIG. 3a.

FIG. 5b shows a side view of the mask frame shown in FIG. 5a.

FIG. 6e shows a view from the patient (rear) side of the mask cushion shown in FIG. 6a.

FIG. 7b shows a view of the clip shown in FIG. 7a.

In FIGS. 6a to 6f and 7a to 7e dimensions are shown in millimeters.

DETAILED DESCRIPTION OF THE INVENTION

The method and apparatus for securing a cushion to a mask frame includes a combination of tongue and groove mechanism and a clip in the form of a collar member which passes over and engages both the cushion and the frame.

Figure 5A:
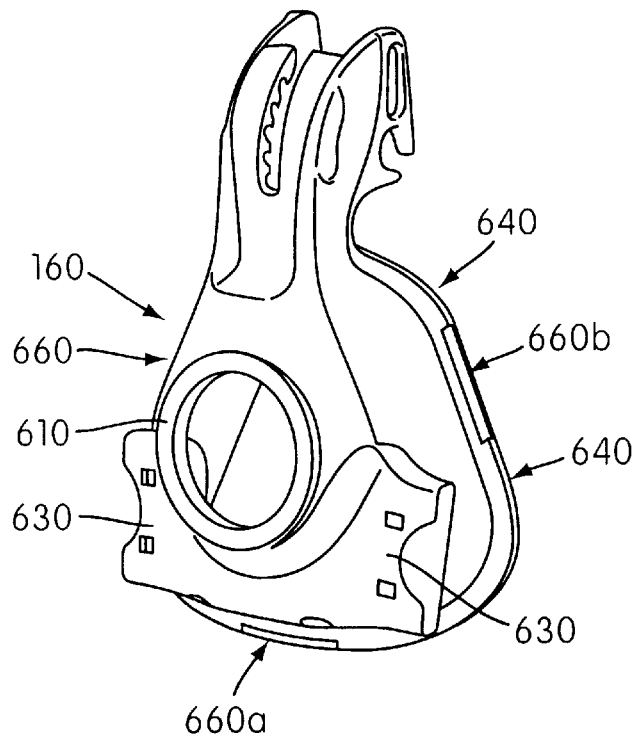
FIG. 5a shows a front perspective view of a nasal mask frame according to an embodiment of the invention.
Figure 5B:
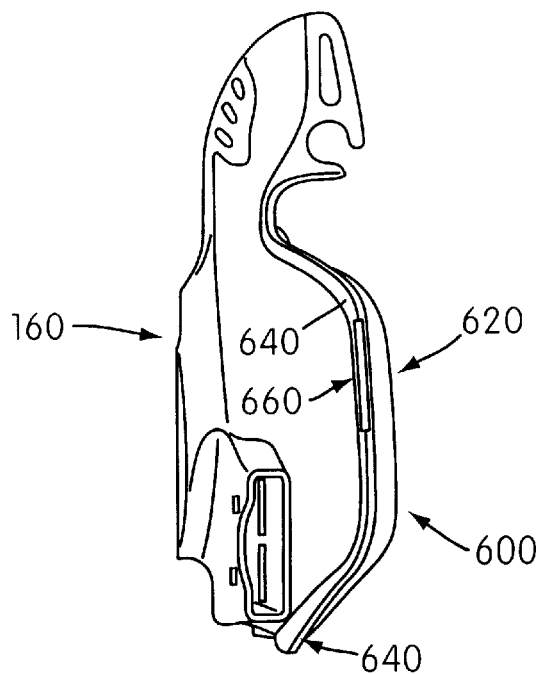
Figure 6C:
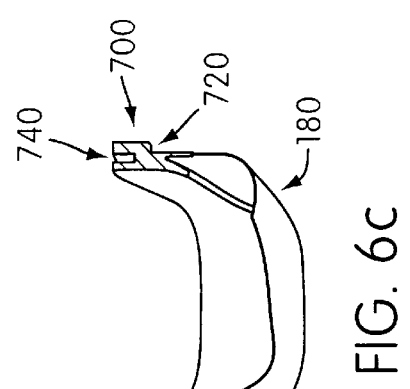
FIG. 6c shows a cross-section through the mask cushion shown in FIG. 6e.
Figure 6F:
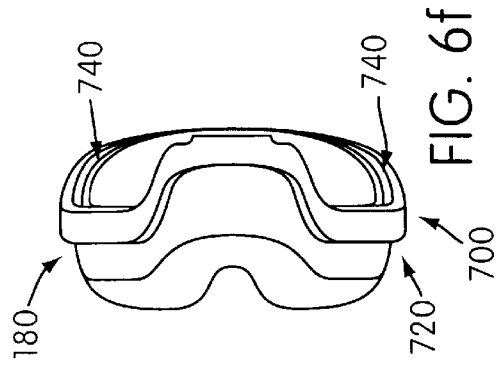
FIG. 6f shows a top view of the mask cushion shown in FIG. 6e.
Figure 6B:
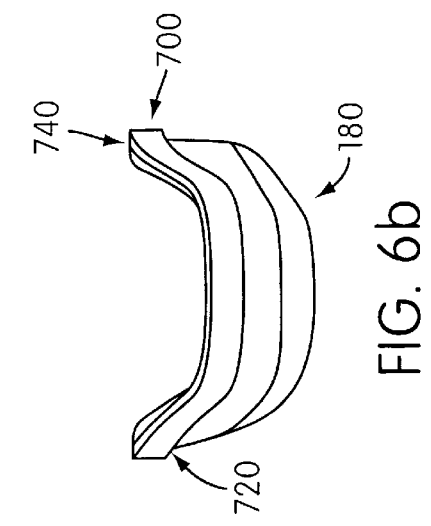
FIG. 6b shows a side view of the mask cushion shown in FIG. 6e.
Figure 6E:
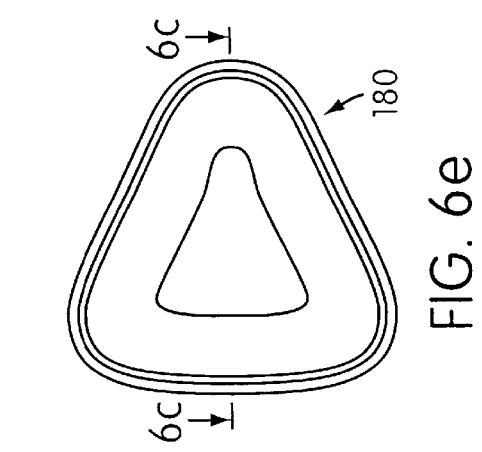
Figure 6A:
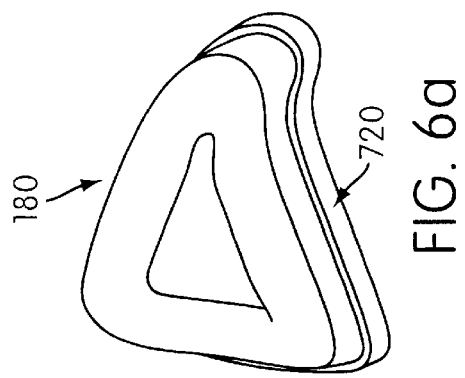
FIG. 6a shows a rear perspective view of a nasal mask cushion suitable for the nasal mask frame of FIGS. 5a and 5b.
Figure 6D:
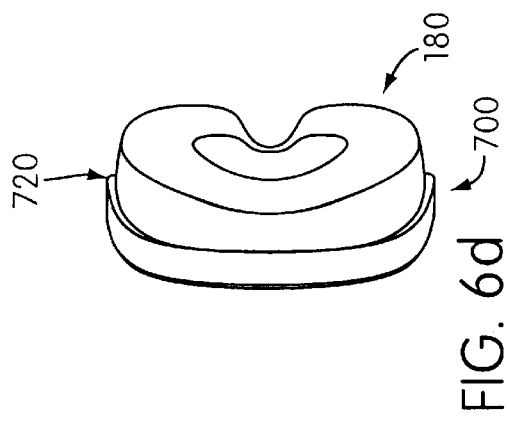
FIG. 6d shows a bottom view of the mask cushion shown in FIG. 6e.
Figure 7E:
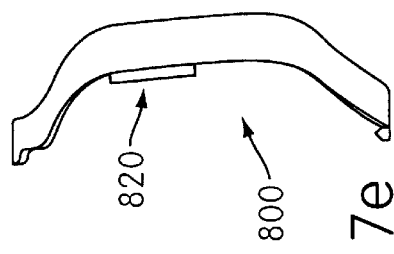
FIG. 7e shows a side view of the clip shown in FIG. 7b.
Figure 7B:
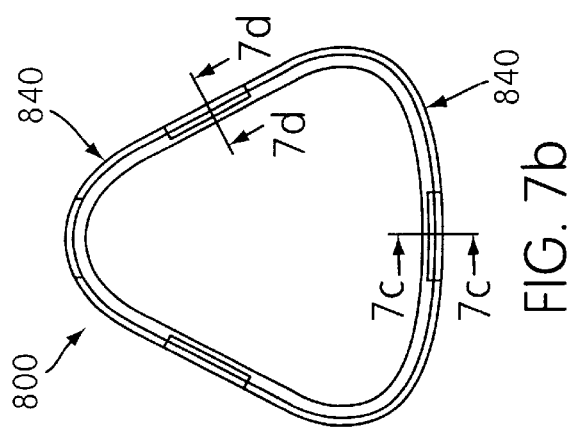
Figure 7D:
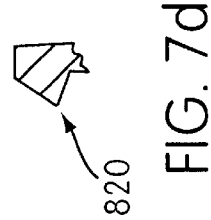
FIG. 7d shows an enlarged section 7d—7d through the clip in the position indicated in FIG. 7b.
Figure 7A:
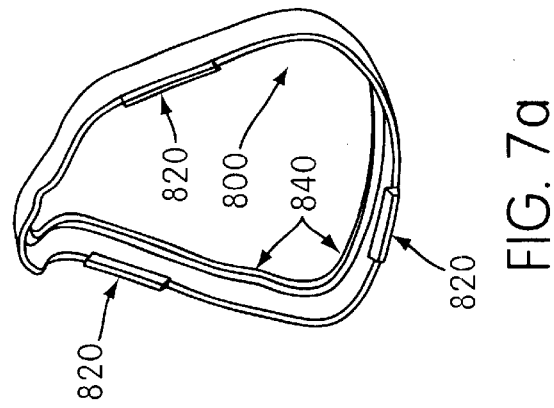
FIG. 7a shows a perspective view of a clip suitable for the nasal mask frame of FIGS. 5a and 5b and the nasal mask cushion of FIGS. 6a to 6f.
Figure 7C:
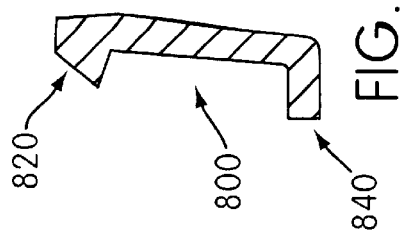
FIG. 7c shows an enlarged section 7c—7c through the clip in the position indicated in FIG. 7b.

A nasal mask frame including a rim portion according to an embodiment of the invention is shown in FIG. 5a and FIG. 5b. The frame (160) is constructed as a substantially rigid shell of polycarbonate or similar transparent plastics material, and incorporates a gas inlet aperture (610) for connection to a gas delivery conduit (not shown) of a patient gas delivery system.

The frame (160) is generally triangular in font view, covering the patient's nose, and defines a cavity which is open at its rear, the rear opening being surrounded by a rim portion (600) which follows a locus approximating the contours of a patient's face.

On the front surface of the frame, are strap connection points (630) for connection of the mask to patient headgear.

As best seen in FIG. 5b, the rim portion (600) of the frame (160) includes a rearwardly projecting tongue (620) and a lateral flange (640). The tongue (620) has an approximately rectangular cross-section. The flange (640) is approximately perpendicular to the tongue (620) and also has an approximately rectangular cross-sectional The flange (640) includes three recesses (660) angularly spaced about the rim. Of these, only the bottom recess (660a) and one side recess (660b) are visible in the view of the (160) shown in FIG. 5a. The recesses are of an approximately rectangular shape, formed in the Font surface of flange (640) adjacent its edge.

A nasal mask cushion including a rim portion (700) according to an embodiment of the invention is shown in FIGS. 6a to 6f. The front edge of the rim portion (700) has a groove (740) which is of complementary shape to and closely receives the tongue (620) of the frame (160).

The thickened rim portion (700) of the cushion has an inwards step (720) in its outer surface, forming a rearwardly facing shoulder.

The cushion is formed of soft material such as silicone, and projects rearwardly of the mask frame so as to space the rigid frame away from the patient's face.

A clip (800) according to an embodiment of the invention, suitable for a nasal mask, is shown in FIGS. 7a to 7e. The clip is formed as a collar of a complementary shape to the rims of the mask cushion (700) and frame (600) and fits over them. The clip is constructed from polycarbonate or similar material. In the illustrated embodiment the clip (800) includes three securing tabs (820) such that inwards projections on the detents are formed as resilient detents which extend past the outer edge of flange (640) to be retained in recesses (660) on the front of the flange (640). To disengage, for example for cleaning of the mask assembly or replacement of the cushion, the detents may be forced outwardly against their natural resilience to release from the recesses (660) and ride over the outer edge of flange (640). In other embodiments, other numbers of securing tabs may be used.

The rear of the clip has an inwards flange (840) which engages behind the shoulder (720) of the cushion so as to hold the cushion securely in position on the frame when the tabs (820) are engaged on the rim (600) of the frame.

Figure 8:
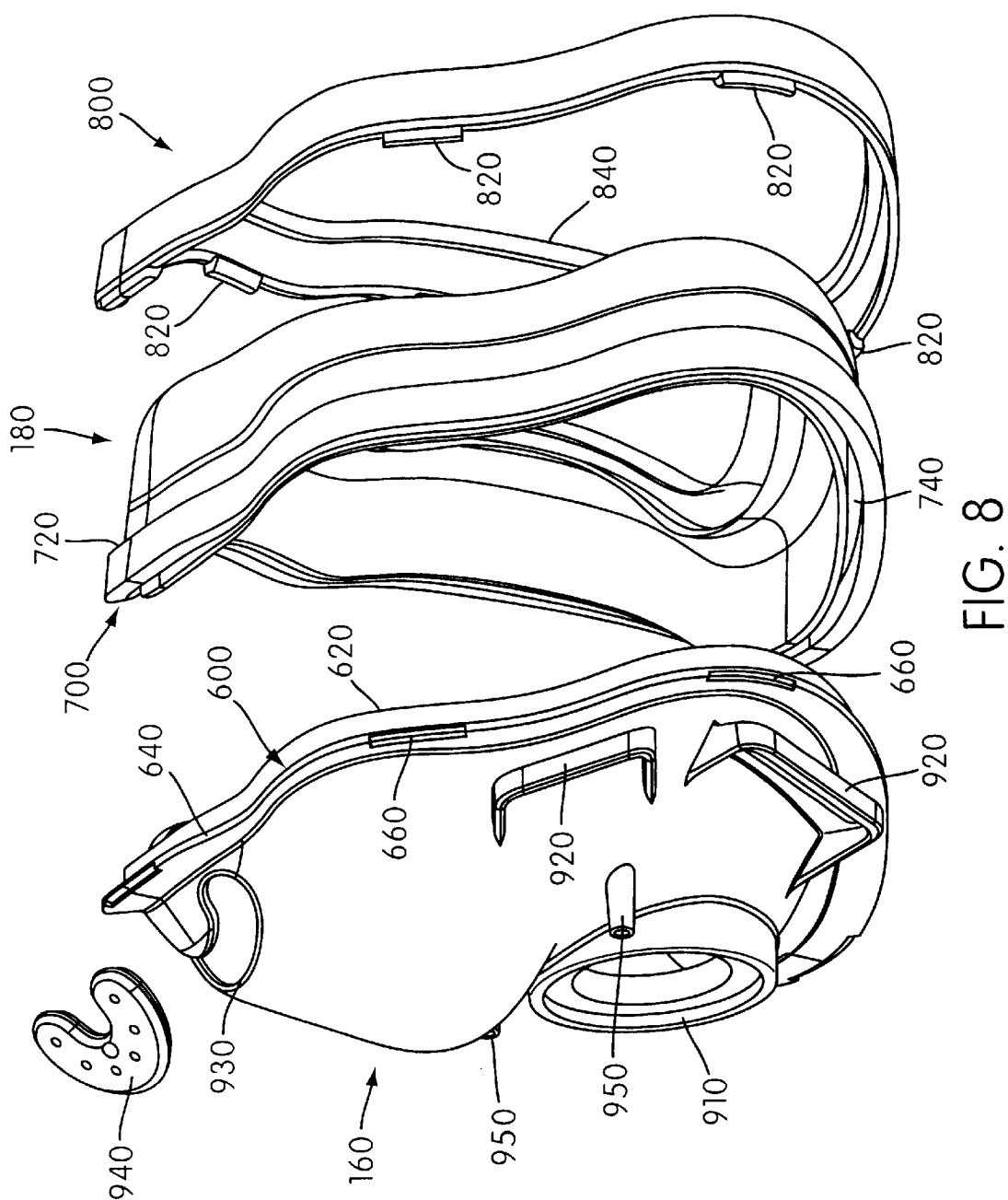
FIG. 8 is an exploded view of an embodiment of the invention as a full-face mask.

The invention is also suitable for a full-face mask system. FIG. 8 shows an exploded view of a Mirage® full-face mask which includes an embodiment of the invention, including a mask frame (160), cushion (180) and clip (800). The frame is adapted to cover both the mouth and nose region of the patient's face, and includes 8 gas inlet aperture (910), connection points (920) for headgear straps, an aperture (930) for receiving an air vent (940) and ports (950).

The interengagement of the clip (800) and respective rim portions (600), (700) of the frame (100) and cushion (180) are similar in principle and construction to those described above with reference to FIGS. 5a, 5b, 6a to 6f and 7a to 7e, except there are six angularly spaced tabs (820) and respective recesses (660). As in the nasal mask assembly, the rim portion (600) of the frame includes a tongue (620) and a lateral flange (640) with recesses in its front surface adjacent its edge, the rim portion (700) of the cushion having a complement groove (740) and rear shoulder surface (720), and the clip having a flange (840) and securing tabs (820) generally as described above for the nasal mask assembly.

FIGS. 9a to 9d illustrate an alternative clipping arrangement. The clip (1000) is again formed generally as a collar, with a rear flange (1020) for engaging the shoulder of the cushion as previously described.

At the base of the clip is a securing hook (1040) which hooks over and engages behind the lateral flange of the mask frame (160), allowing the clip to pivot.

Figure 9A:
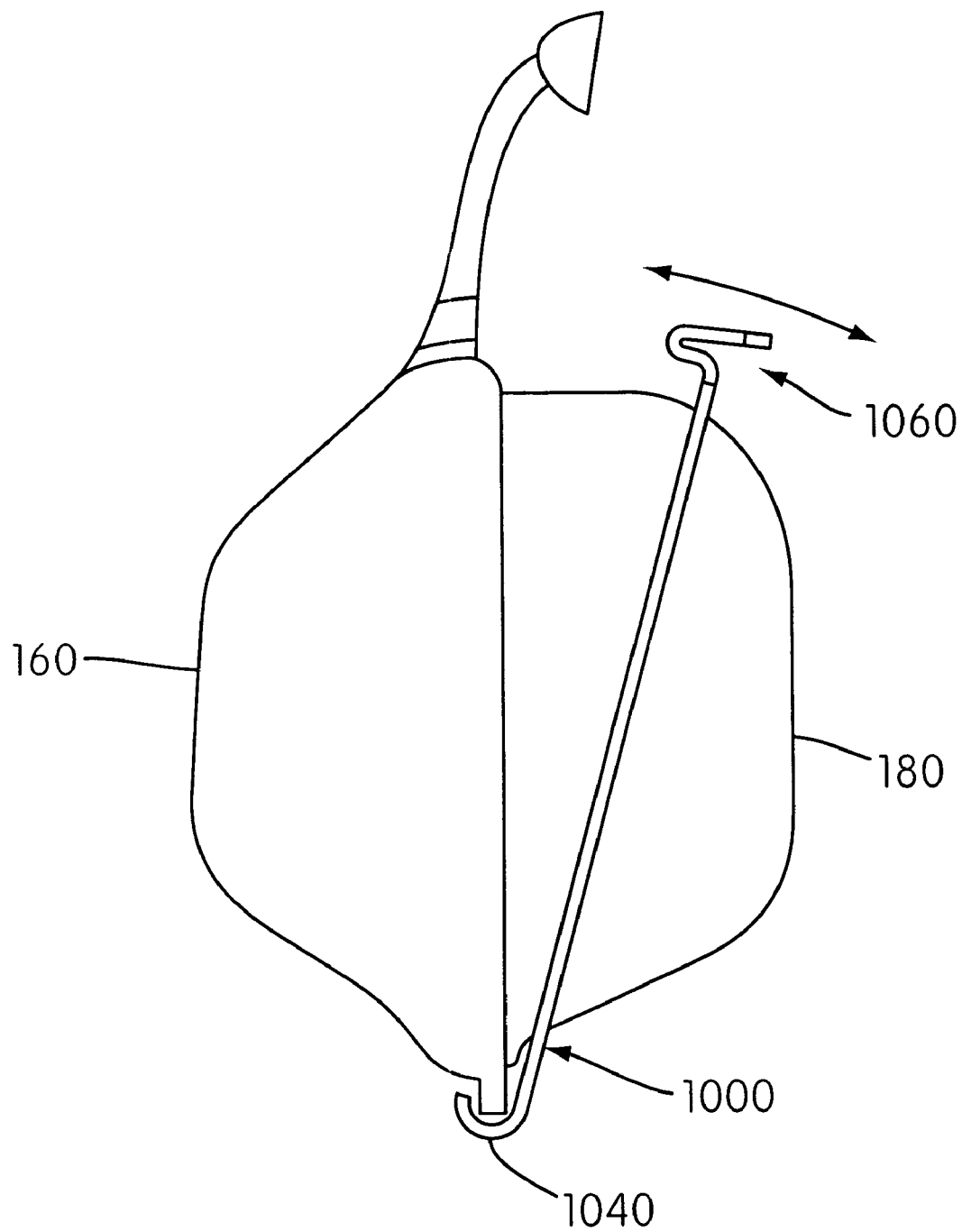
FIG. 9a is a schematic side view of an embodiment employing an alternative clip arrangement.
Figure 9B:
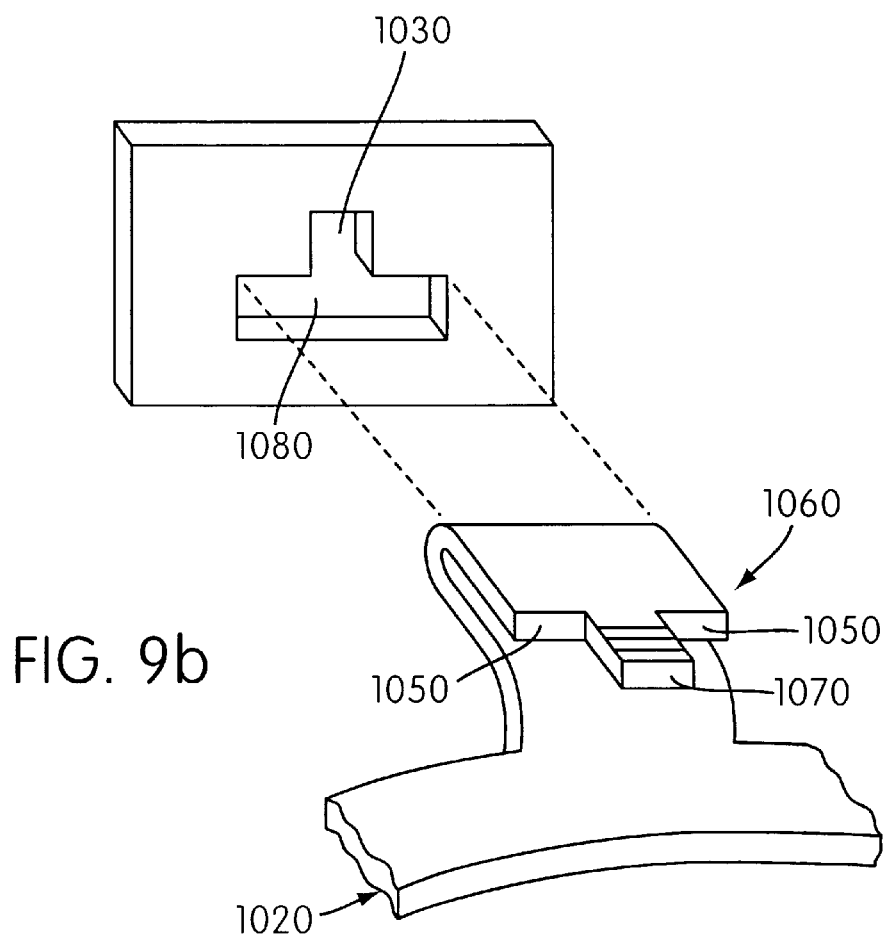
FIG. 9b is a perspective view of engagement of the clip with the mask frame.
Figure 9C:
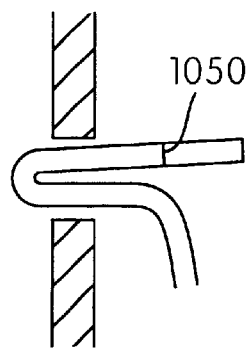
FIGS. 9c and 9d are side views showing clipping of the tab into the slot on the mask frame.
Figure 9D:
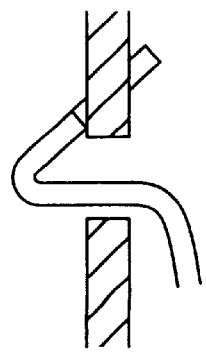

At the top of the clip is a resilient detent arrangement (1060), adapted for engagement with an inverted T-shaped slot (1080) on the upper extension of the mask frame (160) as best shown in FIGS. 9a to 9c.

As shown, the detent is formed as a resilient U-shape with rearwardly facing shoulders (1050) either side of a narrow tab (1070). In use, the clip is pivoted to force the U-shaped detent through the wide part of the T-slot (1080), until the shoulders (1050) clear the rear surface of the slot. The resilience of the detent then forces tab (1070) into the leg (1030) of the T-slot, to retain the clip in position. To disengage the clip, the tab (1070) is depressed to allow the detent to pass back through the slot.

Figure 1:
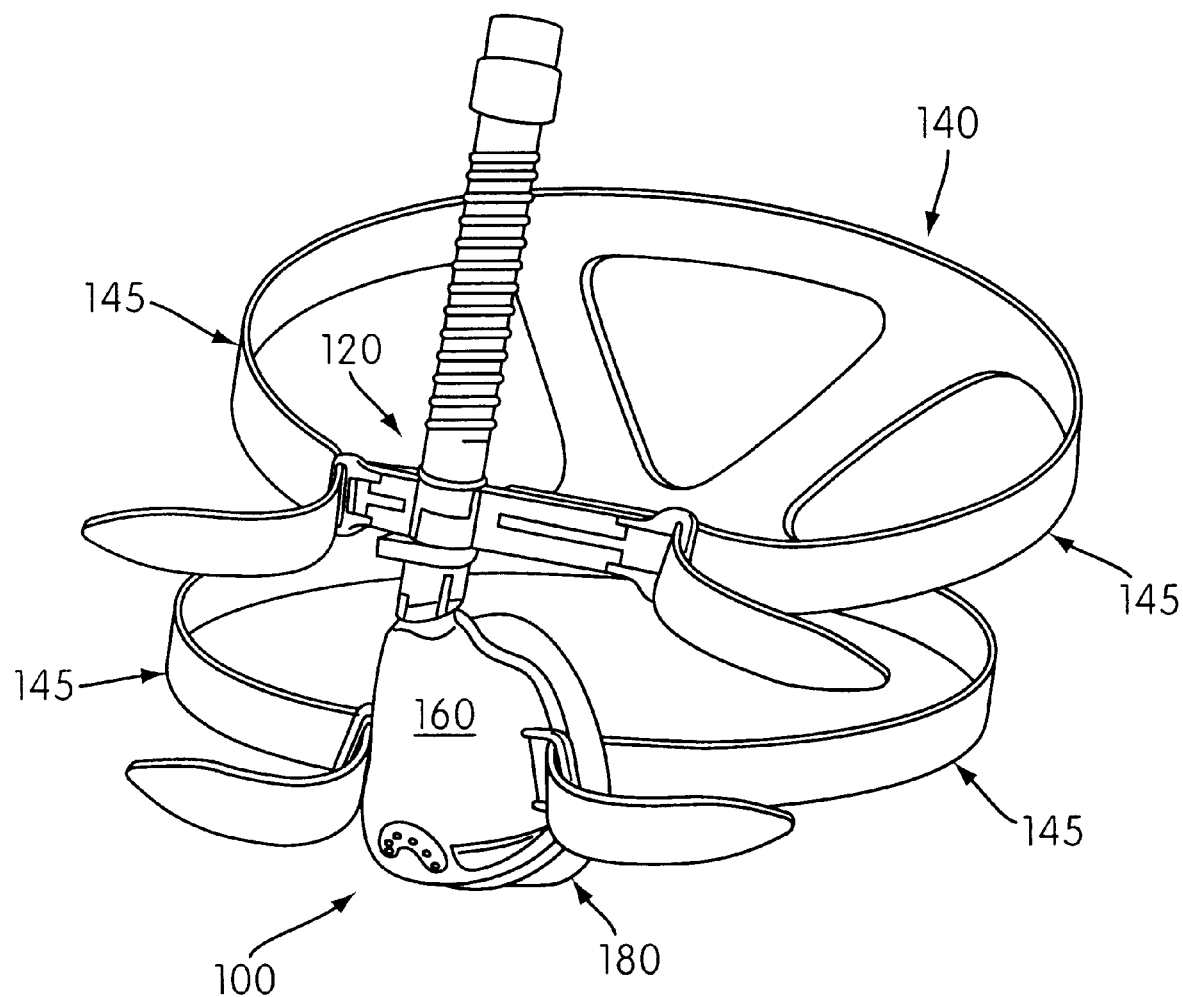
FIG. 1 shows the prior art Mirage® nasal mask system including mask frame, cushion, headgear and forehead support.
Figure 3A:
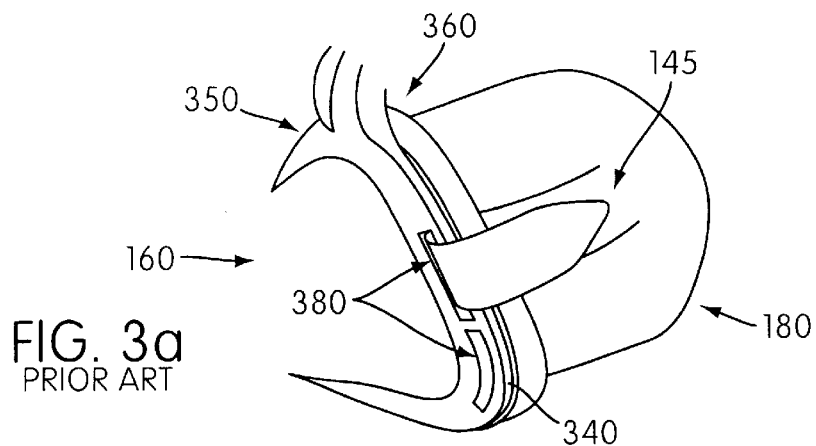
FIG. 3a shows a perspective view of the mask frame and cushion and strap of the prior Gart ResMed Modular Mask System.
Figure 3B:
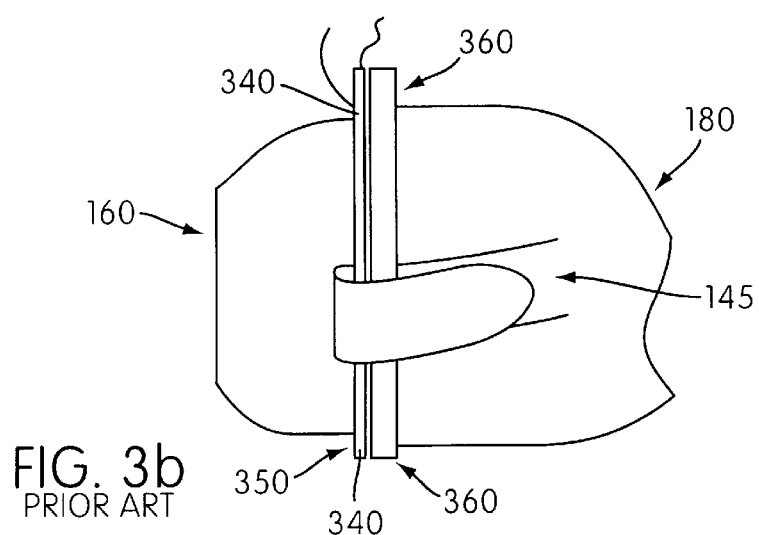
Figure 3C:
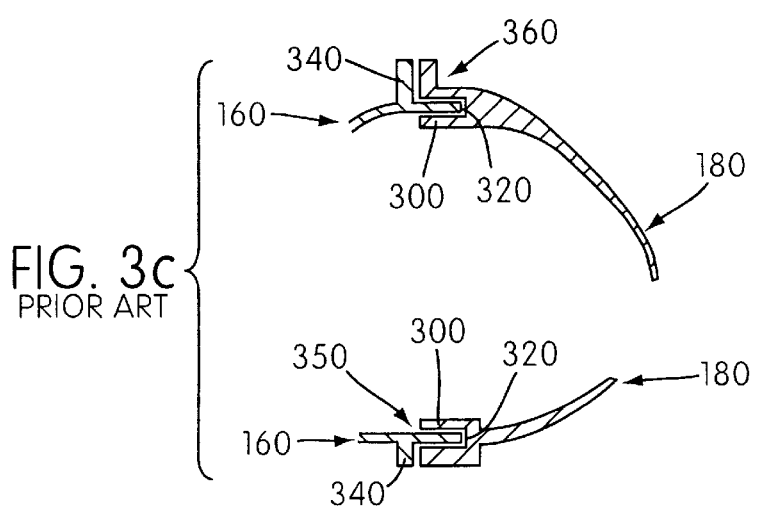
Figure 4A:
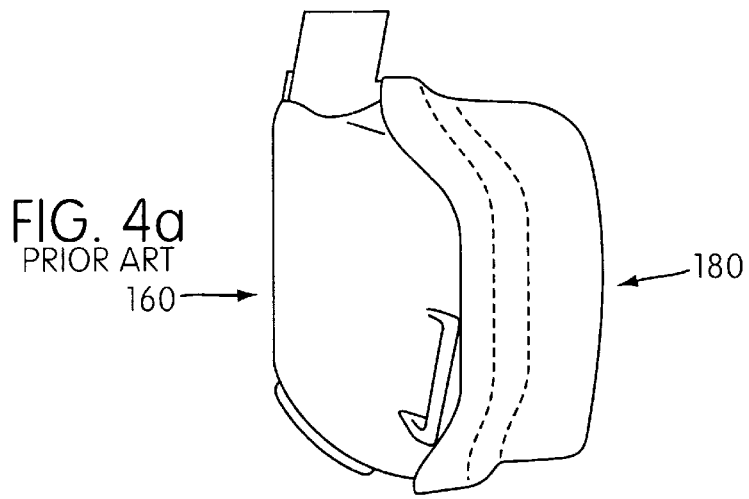
FIG. 4a shows a side view of a prior art mask frame and cushion incorporating a tongue and groove mechanism with an irregular cross-section.
Figure 4B:
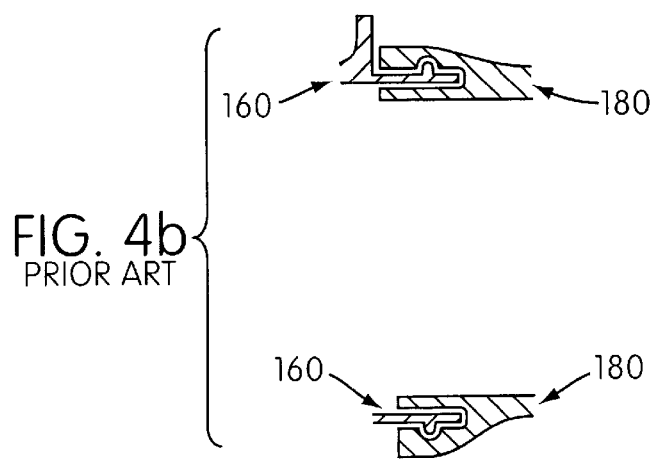
FIG. 4b shows a crosssectional detail of the mask shown in FIG. 4a where the cushion is secured to the frame.
Figure 4C:
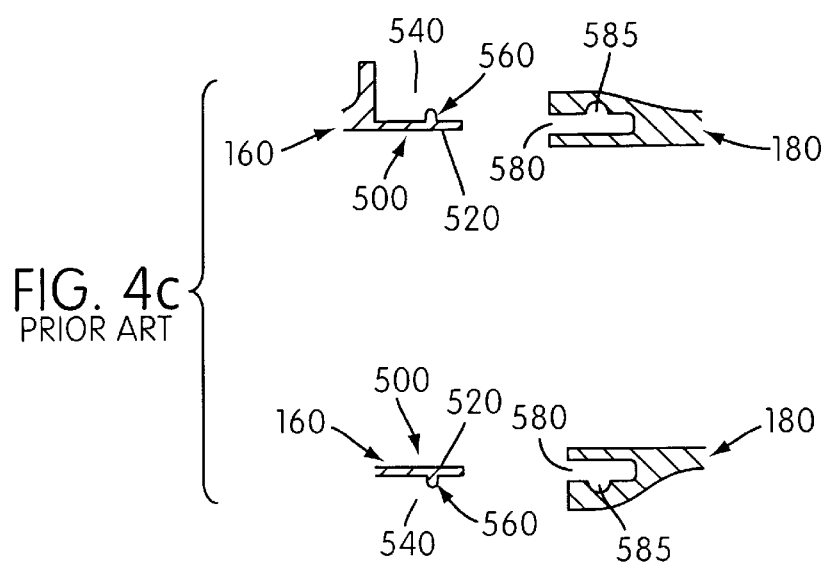
FIG. 4c shows a similar cross-sectional detail of the mask shown in FIG. 4a where the cushion is not secured to the frame.

In an unillustrated embodiment of the invention, the tongue and groove of the frame and cushion have an irregular cross-section, for example as shown in FIGS. 4a to 4c.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

What is claimed is:

1. A respiratory mask assembly for delivering breathable gas to a patient, said mask assembly having a rear side which in use is a patient side of said mask assembly, said mask assembly comprising (i) a substantially rigid mask frame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which includes at least one securing tab which engages a respective recess formed in a lateral flange of said rim portion of said mask frame so as to retain the mask cushion on the mask frame, wherein said securing tab includes a resilient detent which is retained forward of said flange, and wherein said clip member comprises a collar member having a plurality of said tabs and the mask frame includes a respective plurality of said recesses angularly spaced about said rim portion.

2. A respiratory mask assembly according to claim 1 wherein in said mask assembly is a nasal mask and wherein the collar has three of said tabs.

3. A respiratory mask assembly according to claim 1 wherein in said mask is a full face mask and wherein the collar member has six of said tabs.

4. A respiratory mask assembly for delivering breathable gas to a patient, said mask assembly having a rear side which in use is a patient side of said mask assembly, said mask assembly comprising (i) a substantially rigid mask frame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which engages the mask frame so as to retain the mask cushion on the mask frame, wherein the clip member comprises a collar member having first securing means which engages the mask frame and allows pivoting of the clip to a position at which second securing means clips into engagement with the mask frame.

5. A respiratory mask assembly for delivering breathable gas to a patient, said mask assembly having a rear side which in use is a patient side of said mask assembly, comprising (i) a substantially rigid mask frame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having a cushion retainer to engage behind said shoulder of the cushion and a frame retainer to engage the mask frame so as to retain the mask cushion on the mask frame, wherein said clip member comprises a collar member having a plurality of securing tabs which engage a respective plurality of recesses in the mask frame, said recesses being angularly spaced about said rim portion.

* * * * *

UNITED STATES PATENT AND TRADEMARK OFFICE
CERTIFICATE OF CORRECTION

PATENT NO. : 6,412,487 B1
DATED : July 2, 2002
INVENTOR(S) : Gunaratnam et al.

It is certified that error appears in the above-identified patent and that said Letters Patent is hereby corrected as shown below:

Title page,
Item [63], should read:
-- [63] Continuation-in-Part (CIP) of U.S. Patent Application No. 09/498,705, filed February 7, 2000, pending; a CIP of U.S. Patent Application No. 09/316,227, filed May 21, 1999, pending; a CIP of U.S. Design Patent Application No. 29/101,860, filed 12 March 1999, now U.S. Design Patent No. D428,139; a CIP of U.S. Design Patent Application No. 29/101,861 filed March 12, 1999, now U.S. Design Patent No. D430,663; a CIP of U.S. Design Patent Application No. 29/101,862 filed March 12, 1999, now U.S. Design Patent No. D428,988; and a CIP of U.S. Design Patent Application No. 29/115,618 filed December 16, 1999, now U.S. Design Patent No. D443,355. --

Item [30], should read:
-- Foreign Application Priority Data
Dec. 9, 1998 (AU) ..................................................... 3922/1998
Dec. 9, 1998 (AU) ..................................................... 3923/1998
Dec. 9, 1998 (AU) ..................................................... 3924/1998
Feb. 9, 1999 (AU) ..................................................... PP8550
Jun. 18, 1999 (AU) .................................................... PQ1029
Jun. 18, 1999 (AU) .................................................... PQ1040
Jun. 18, 1999 (AU) .................................................... 1916/1999 --

Column 1,
Lines 3-16, should read:
This application is a Continuation-in-part (CIP) of U.S. patent application Ser. No. 09/498,705, filed Feb. 7, 2000, currently pending; a CIP of U.S. patent application Ser. No. 09/316,227, filed May 21, 1999, currently pending; a CIP of U.S. Design patent application Ser. No. 29/101,860, filed 12 Mar. 1999, now U.S. Design Pat. No. D428,139; a CIP of U.S. Design patent application Ser. No. 29/101,861 filed Mar. 12, 1999, now U.S. Design Patent No. D430,663; a CIP of U.S. Design patent application Ser. No. 29/101,862 filed Mar. 12, 1999, now U.S. Design Patent No. D428,988;

UNITED STATES PATENT AND TRADEMARK OFFICE
CERTIFICATE OF CORRECTION

PATENT NO. : 6,412,487 B1
DATED : July 2, 2002
INVENTOR(S) : Gunaratnam et al.

It is certified that error appears in the above-identified patent and that said Letters Patent is hereby corrected as shown below:

Column 1 (cont'd),
and a CIP of U.S. Design Patent Application Ser. No. 29/115,618 filed December 16, 1999, now U.S. Design Patent No. D443,355 the disclosures of which are hereby incorporated by reference. --

Signed and Sealed this

Thirtieth Day of September, 2003

JAMES E. ROGAN
*Director of the United States Patent and Trademark Office*